United States Patent [19]
Peszynski

[11] Patent Number: 5,598,846
[45] Date of Patent: Feb. 4, 1997

[54] ROTATABLE ULTRASOUND TRANSDUCER FINGER PROBE

[75] Inventor: Michael Peszynski, Newburyport, Mass.

[73] Assignee: Hewlett-Packard Company, Palo Alto, Calif.

[21] Appl. No.: 576,659

[22] Filed: Dec. 21, 1995

[51] Int. Cl.⁶ ..................................................... A61B 8/12
[52] U.S. Cl. ................................. 128/662.06; 128/660.08
[58] Field of Search ......................... 128/660.08, 660.09, 128/660.1, 661.01, 662.03, 662.04, 662.06

[56] References Cited

U.S. PATENT DOCUMENTS 4,543,960  10/1985  Harui et al. .
4,869,260   9/1989  Young et al. ...................... 128/662.04
5,088,500   2/1992  Wedel et al. ...................... 128/662.06
5,152,293  10/1992  Vonesh et al. ..................... 128/662.04
5,181,514   1/1993  Solomon et al. .
5,284,147   2/1994  Hanaoka et al. ................... 128/662.06

Primary Examiner—George Manuel
Attorney, Agent, or Firm—John L. Imperato

[57] ABSTRACT

A rotatable finger probe provides rotation of an image plane about an image axis in interoperative and intra cavity ultrasound imaging applications. A finger clip attaches the rotatable finger probe to a physician's finger and by movement of the finger, the imaging axis is aimed at a patient's body part to be imaged. Once the image axis is aimed at the patient's body part, rotation of the image plane by the rotatable finger probe is activated remotely.

12 Claims, 2 Drawing Sheets

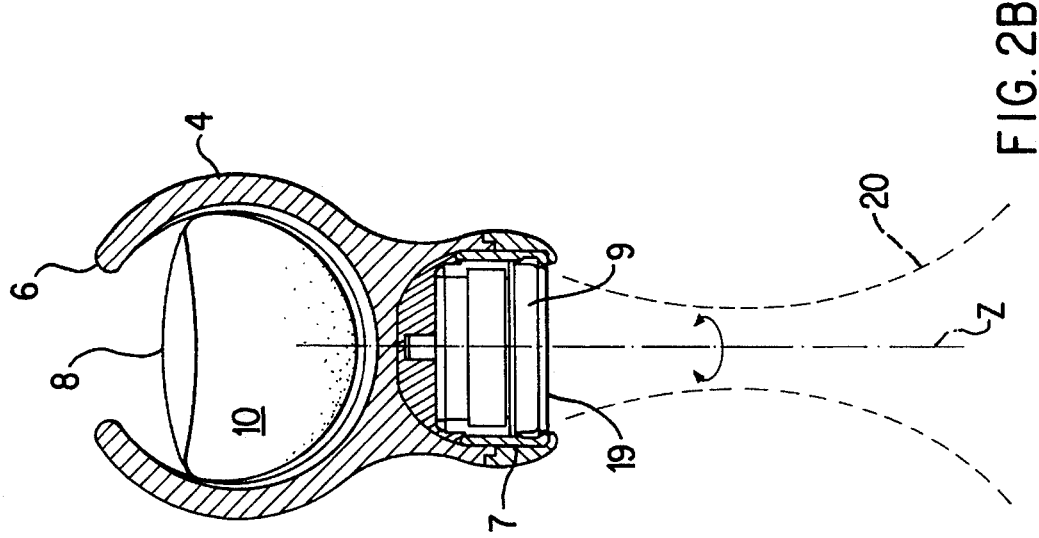
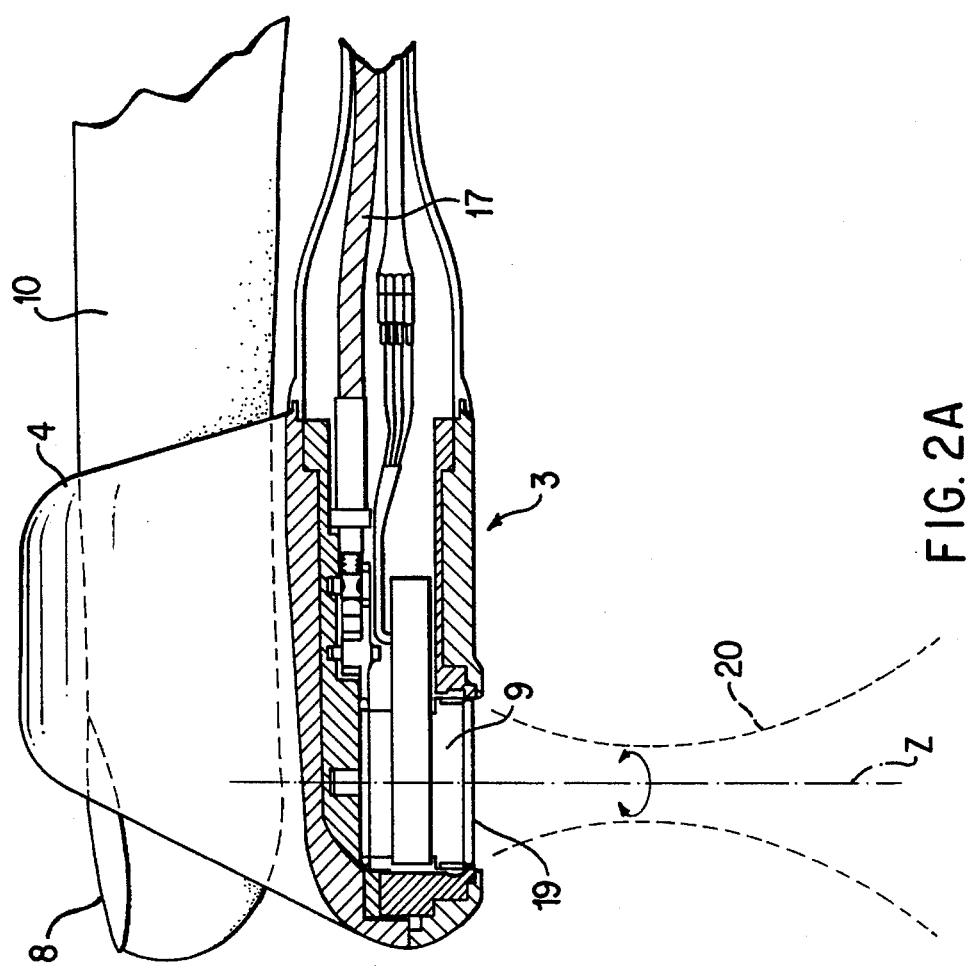
FIG. 2B
FIG. 2A

5,598,846

ROTATABLE ULTRASOUND TRANSDUCER FINGER PROBE

FIELD OF THE INVENTION

This invention discloses a rotatable ultrasound transducer probe that can be attached to a physician's finger for use in interoperative ultrasound imaging applications.

BACKGROUND OF THE INVENTION

Rotatable ultrasound transducer probes, such as transesophageal or TEE probes, are used for viewing planar ultrasound images of a patient's heart from inside of the patient's esophagus. The tip of the TEE probe houses a rotatable array element. Rotation of the array element causes a corresponding rotation of the image plane about an image axis. Once the TEE probe is inserted down the esophagus, rotation of the array element is controlled at a remote distance from the probe tip. TEE probes are described by Solomon et al. in U.S. Pat. No. 5,181,514 and Harui et al. in U.S. Pat. No. 4,543,960.

In contrast to TEE probes, in which rotation of the image plane is controlled at a remote distance from the probe tip, finger probes are attached to a physician's finger. The image plane orientation is then manually controlled by the movement of the physician's finger. Finger probes are well suited for internal imaging through the body cavities and in interoperative environments during open heart surgery or vascular surgery. One type of finger probe taught by Hanaoka et al. in U.S. Pat. No. 5,284,147 uses a stationary imaging element. While the image axis of the stationary imaging element may be readily aimed at the patient's body part to be viewed, rotation of the image plane about the image axis to obtain other critical views of the patient's body part is implemented by physically rotating the finger probe and its attached cable. Since the body cavities into which the finger probe is inserted, are often small and space constrained, physical rotation of the finger probe is limited, which reduces viewing access to the patient's body parts.

SUMMARY OF THE INVENTION

In the preferred embodiment of the present invention, a rotatable finger probe uses a rotatable array element to achieve rotation of an image plane for use in interoperative and intra cavity ultrasound imaging applications. A finger clip provides attachment of the rotatable finger probe to a physician's finger which allows the finger to aim the imaging axis at a patient's body part. A foot switch or other remote control mechanism controls rotation of the image plane about an image axis for acquisition of various views of the patient's body. The rotatable finger probe combines the benefit of precise aiming of the image axis inherent to known finger probes with the remote control of the image plane rotation provided by transesophageal type probes.

BRIEF DESCRIPTION OF THE DRAWINGS

FIGS. 2A and 2B shows detailed views of the rotatable ultrasound finger probe.

DETAILED DESCRIPTION OF THE PREFERRED EMBODIMENT

Figure 1:
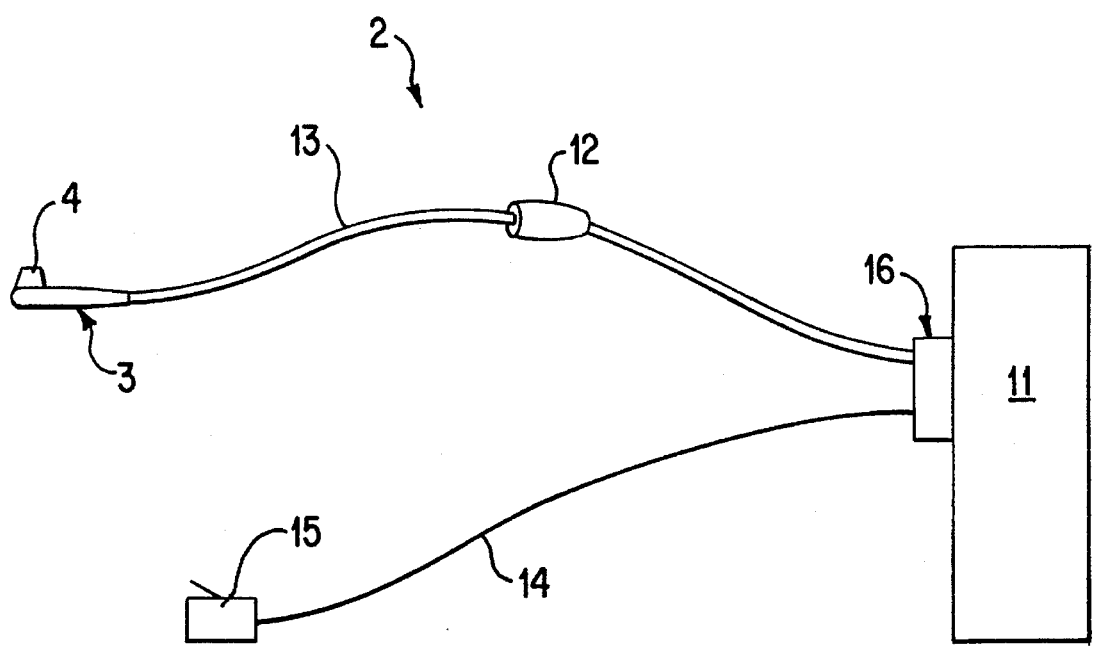
FIG. 1 shows a rotatable ultrasound finger probe system of the present invention.

FIG. 1 shows an ultrasound probe system 2 of the present invention. Rotatable finger probe 3, hereinafter probe 3, is attached to the finger of a physician or technician by a finger clip 4. Depending on the patient's body part to be viewed, the finger and attached probe 3 are inserted into one of the patient's natural body openings or into a patient's body cavity that has been opened as a result of surgery. For example, during open heart surgery, the functionality of the heart and blood flow in the arteries may be monitored using ultrasound images produced by the ultrasound probe system 2. A cable 13 connects probe 3 to a system display unit 11 through connector 16. A motor 12, which controls the rotational orientation of the ultrasound images relative to the patient's body part, is activated by a foot switch 15 or alternatively, via controls on the system display unit 11. Foot switch 15 is connected to the system display unit 11 via control cable 14.

FIG. 2 shows detailed views of the rotatable finger probe 3, or probe 3, of the present invention. FIG. 2A shows the side view of the finger 10 inserted through finger clip 4 of the probe 3. The clip 4 may be fabricated from plastic, rubber or other suitably deformable material. The clip 4 becomes slightly deformed as the finger is inserted into the clip 4. The resistance of the clip 4 to the slight deformation supplies enough pressure to the finger 10 to firmly hold the probe 3 on the finger 10. The clip 4 also has an open top 6, as shown in FIG. 2B, to permit quick withdrawal of the finger 10 from the clip 4 in critical situations in which the physician quickly needs to use both hands for another task. The clip 4 also has a streamlined tape and has rounded edges so as to minimize irritation to the body cavity into which probe 3 is inserted.

The finger 10 is oriented in clip 4 such that the fingernail 8 is opposite a rotatable array element 9. The rotatable array element 9 is within a housing 7 and is positioned behind a stationary acoustic window 19. Rotational coupling between the motor 12 and the rotatable array element 9 is provided by drive shaft 17. Rotational drive mechanisms are known in the art.

Using an electrical signal produced by the system display unit 11, the rotatable array element 9 emits an ultrasound beam 20 that is scanned back and forth. The scanned ultrasound beam 20 defines an image plane that contains an image axis Z. This scanning can be performed electronically or mechanically, as both are well known in the art. The ultrasound beam 20 interacts with the patient's body part and is received by the system display unit 11 and used to produce a planar cross-sectional ultrasound image of the patient's body part which is shown on a display of the system display unit 11. The probe 3 can be precisely aimed by the physician using the finger 10 and by directing the image axis Z at the body part of interest. Once the image axis Z is aimed, the image plane is then rotated about the image axis Z (indicated by the arrows) by remote activation of motor 12.

Rotation of the image plane is especially desirable in interoperative imaging applications in which various imaging planes can not be accessed by simply changing the rotational orientation of the probe 3 and finger 10 due to space constraints of the imaging environment. Often space constraints limit the maneuverability of the probe 3 once it is inserted into a patient's body. A variety of views of the patient's body part are obtained from a single positioning on the probe 3 of the present invention. Through rotation of the image plane via the rotatable array element 9 positioned behind a stationary acoustic window 19, the rotatable finger probe 3 provides the benefit of precise aiming of the image axis Z, while providing image plane rotation as the rotatable finger probe is held stationary.

I claim:

1. A rotatable finger probe, comprising:

a housing;

a rotatable array element within the housing, the array element producing an ultrasound beam;

a finger clip joined to the housing, providing attachment to an operator's finger; and means for rotating the array element wherein rotation of the array element correspondingly rotates the ultrasound beam relative to the housing.

2. The rotatable finger probe of claim 1 wherein the ultrasound beam produced by the array element comprises a planar ultrasound beam having an image axis, and wherein rotation of the array element rotates the planar ultrasound beam about the image axis.

3. The rotatable finger probe of claim 2 wherein the means for rotating comprises a rotating drive shaft.

4. The rotatable finger probe of claim 3 further comprising a stationary acoustic window attaching to the housing.

5. The rotatable finger probe of claim 4 wherein the finger clip attaches the probe to the physician's finger, on a side of the operator's finger opposite the finger nail.

6. The rotatable finger probe of claim 4 wherein the drive shaft is controlled by a foot switch.

7. A system for ultrasonically interrogating a patient's body parts accessible through the natural body cavities and accessible interoperatively, and for producing a series of ultrasound images based on the interrogation, the system comprising:

an ultrasound probe, producing a planar ultrasound beam having an image axis, and receiving reflections of the beam by a patient's body parts;

a finger clip providing attachment of the probe to a physician's finger;

a rotatable array element within the ultrasound probe, rotating the planar ultrasound beam as the ultrasound probe is held stationary; and a display unit, displaying ultrasound images based on the ultrasound beam produced and the reflections received.

8. The system of claim 7 wherein each rotational position of the array element corresponds to a two-dimensional ultrasound image of the patient's body parts.

9. The system of claim 8 further comprising a cable connecting the ultrasound probe to the display unit.

10. The system of claim 9 further comprising a drive shaft, within the cable, providing rotation of the rotatable array element.

11. The system of claim 10 further comprising a foot switch controlling the drive shaft.

12. The system of claim 10 wherein the drive shaft is controlled via controls on the front panel of the display unit.

\* \* \* \* \*